United States Patent [19]
Waterman et al.

[11] Patent Number: 5,627,749
[45] Date of Patent: May 6, 1997

[54] CORROSION MONITORING TOOL

[75] Inventors: David K. Waterman, Chino, Calif.;
Steven W. Powell, Houston, Tex.;
Budd Sweetman, Fontana; Walter J. Maciejewski, Newport Beach, both of Calif.

[73] Assignee: Rohrback Cosasco Systems, Inc., Santa Fe Springs, Calif.

[21] Appl. No.: 201,838

[22] Filed: Feb. 25, 1994

[51] Int. Cl.$^6$ .................................................. G01N 17/04
[52] U.S. Cl. .......................... 364/422; 166/902; 73/152.01
[58] Field of Search ...................... 73/151, 155; 324/71.2; 166/336, 902; 364/422

[56] References Cited

U.S. PATENT DOCUMENTS

| | | |
|---|---|---|
| 2,703,053 | 3/1955 | Castel . |
| 2,940,177 | 6/1960 | Bricaud . |
| 3,104,355 | 9/1963 | Holmes et al. . |
| 3,588,908 | 6/1971 | Lindsey . |
| 3,609,549 | 9/1971 | Hausler et al. . |
| 3,616,415 | 10/1971 | Watson et al. . |
| 3,766,042 | 10/1973 | Wilson . |
| 3,999,121 | 12/1976 | Taylor, Jr. . |
| 4,161,782 | 7/1979 | McCracken ............................. 364/571 |
| 4,217,544 | 8/1980 | Schmidt . |
| 4,226,693 | 10/1980 | Maes . |
| 4,338,097 | 7/1982 | Turner . |
| 4,338,563 | 7/1982 | Rhoades et al. .................... 324/65 CR |
| 4,354,553 | 10/1982 | Hensley . |
| 4,380,763 | 4/1983 | Peart et al. . |
| 4,393,598 | 7/1983 | Powell et al. . |
| 4,501,323 | 2/1985 | Lively et al. . |
| 4,587,479 | 5/1986 | Rhoades et al. .................... 324/65 CR |
| 4,603,113 | 7/1986 | Bauer . |
| 4,605,065 | 8/1986 | Abercrombie . |
| 4,688,638 | 8/1987 | Williams . |
| 4,755,744 | 7/1988 | Moore et al. . |
| 4,806,153 | 2/1989 | Sakai et al. ................................ 73/151 |
| 4,866,607 | 9/1989 | Anderson et al. ....................... 364/422 |
| 4,928,760 | 5/1990 | Freitas . |
| 4,945,761 | 8/1990 | Lessi et al. ................................. 73/151 |
| 5,095,977 | 3/1992 | Ford . |
| 5,130,705 | 7/1992 | Allen et al. ........................... 340/853.9 |
| 5,136,525 | 8/1992 | Cloud ...................................... 364/550 |
| 5,171,517 | 12/1992 | Solomon et al. . |
| 5,171,524 | 12/1992 | Niolon . |
| 5,243,297 | 9/1993 | Perkins et al. . |
| 5,525,976 | 6/1996 | Balgard ................................. 340/870.17 |
| 5,529,668 | 1/1996 | Hall ...................................... 205/776.5 |
| 5,532,128 | 1/1996 | Eggers et al. ............................. 435/16 |

FOREIGN PATENT DOCUMENTS

| | | |
|---|---|---|
| 2150300 | 6/1985 | United Kingdom . |
| 2266379 | 10/1993 | United Kingdom . |
| WO9409354 | 4/1994 | WIPO . |

*Primary Examiner*—Gail O. Hayes
*Attorney, Agent, or Firm*—Renner, Otto, Boisselle, Sklar

[57] ABSTRACT

A tool for monitoring corrosion levels within a wellbore particularly suited for remote monitoring over extended periods. The monitoring tool utilizes a thin wall electrical resistance type corrosion sensor to determine rate of metal loss within the wellbore. The corrosion sensor is preferably made of the same material as the production tubing or drill pipe of the well and is positioned to allows the fluid within the wellbore to flow over the sensor at the same rate as the fluid flows over the tubing. A reference element is incorporated into the corrosion sensor to provide primary temperature compensation. A temperature sensor provides temperature data and allows for secondary temperature compensation for the corrosion sensor. A central processing unit reads and stores the data from the three sensors into solid state memory. The probe records data at programmable time intervals. Upon retrieval of the probe from the wellbore, the probe may be connected to a computer for downloading of the raw data and subsequent analysis.

16 Claims, 4 Drawing Sheets

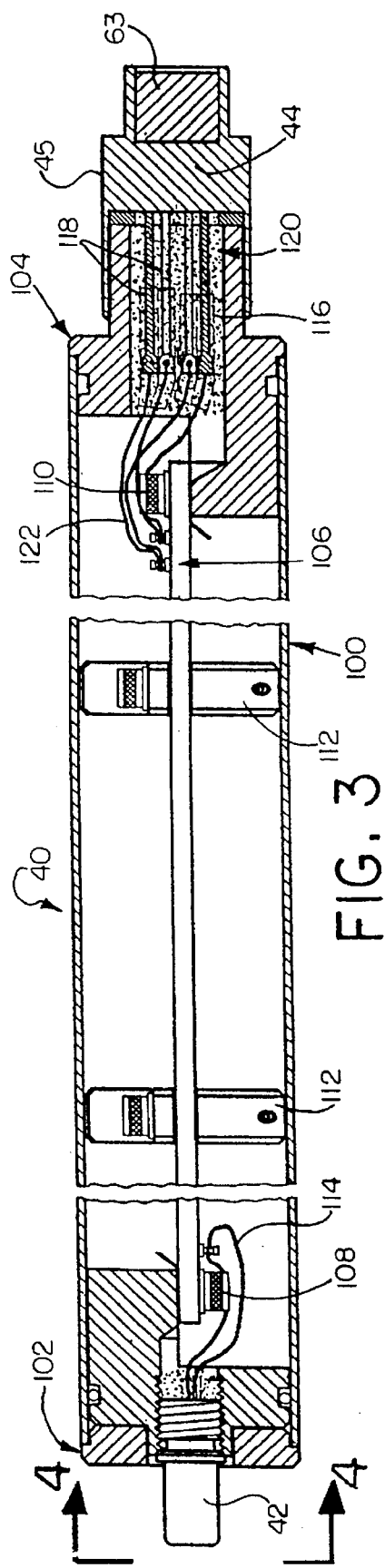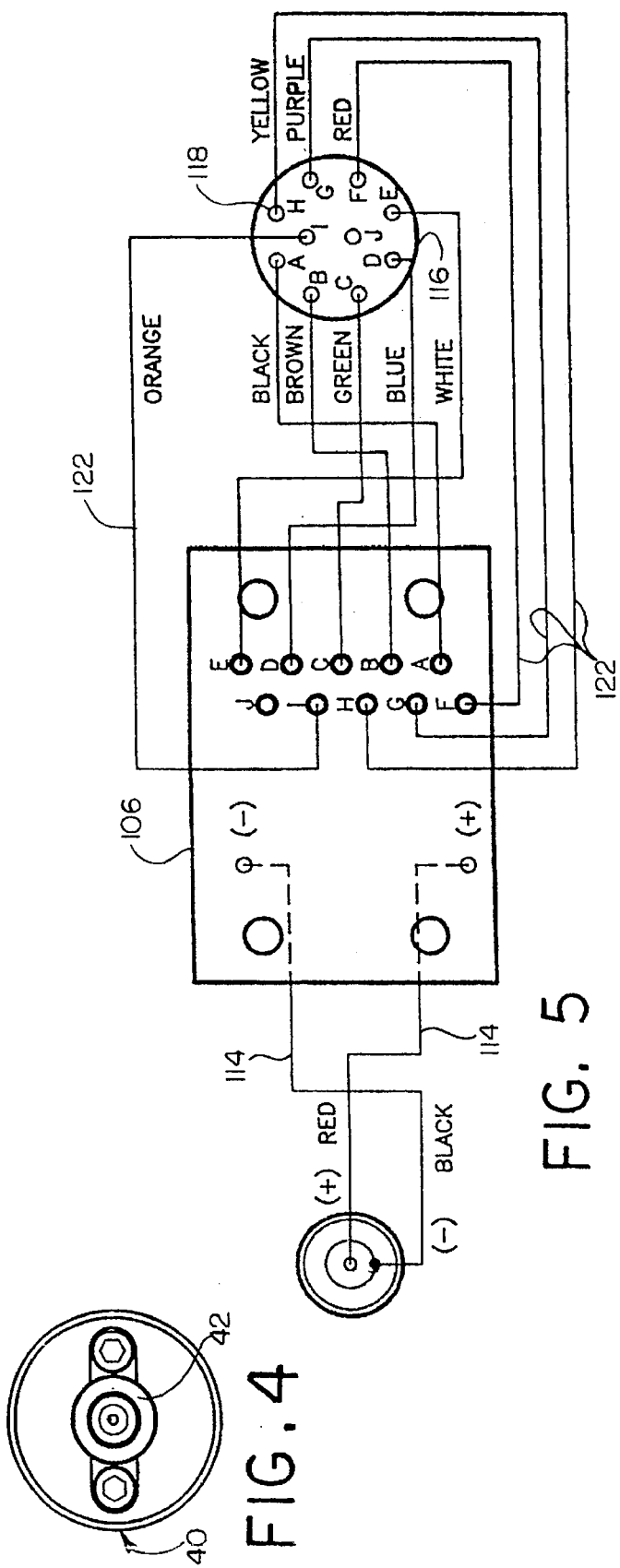

CORROSION MONITORING TOOL

BACKGROUND OF THE INVENTION

1. Field of the Invention

This invention relates to a tool for monitoring corrosion within a wellbore and, in particular, to a stand-alone downhole monitoring probe which records and stores corrosion data over an extended period for subsequent downloading and analysis upon retrieval of the tool.

2. Description of the Prior Art

During the drilling of an oil and gas or geothermal well, carbon dioxide and hydrogen sulfide gases react with water to form carbonic acid and hydro-sulfuric acid, respectively. Within the temperature and pressure condition of a well, these acids can create pH levels of approximately 4.0. The corrosive attack on the drill pipe or production tubing upon completion of the well can be very aggressive. Potentially corrosive environments in oilfield drilling and production operations are addressed by utilizing drill pipe and production tubing manufactured from corrosion resistant alloys or carbon steel materials in conjunction with corrosion inhibitor treatment programs. Since corrosion may occur at different rates from the wellbore perforations to the surface due to pressure, temperature, fluid density or velocity, a corrosive inhibitor which performs effectively at one depth may not be optimum for another depth. A means of accurately determining the corrosion at various depths allows corrosion inhibitors to be evaluated for effectiveness and optimum inhibitor flow rates.

One apparatus which has been used for corrosion monitoring is the "weight loss coupon". A coupon is a precisely machined piece of metal of the same or similar material as the pipe or lining. It is positioned within the flow of the fluid at a point where corrosion is to be monitored. The coupon remains there for a long enough period of time for some corrosion to occur (possibly a month or more) at which point the coupon is retrieved. The coupon is weighed and from the resulting weight loss the amount of cumulative corrosion over the exposure period can be determined. While this is an economical and accurate method of determining corrosion rates, it only gives average corrosion rates over the exposure period. Variations in the corrosion rate over the period cannot be determined. A method for determining the time related corrosion history can be an important tool to allow various corrosion inhibitors to be tried at varying flow rates to determine the optimum inhibitor and flow rate to minimize corrosion and costs.

Various alternative methods have been employed to monitor the metal loss over a predetermined period of time within the wellbore. Electrical resistance measuring elements have been employed but lack a reference element for accurate readings. Such resistance temperature devices are not used for discrete temperature measurements for compensation within the electrical measurement. Prior known systems have also attempted to utilize linear probe resistance technology with little success. Still other systems utilize electrochemical means of detecting when a corrosive fluid is present in a pipeline which normally contains a non-corrosive fluid. Since most wellbores contain corrosive environments it is the rate of corrosion which needs to be determined over a given period of time.

SUMMARY OF THE PRESENT INVENTION

The present invention overcomes the disadvantages of the prior known corrosion monitoring systems by providing a downhole instrument pack with memory for data storage and an external electrical resistance corrosion sensor. The data is downloaded from the central processing unit of the tool for analysis.

The corrosion monitoring tool of the present invention must be suitable for placement within the corrosive environment of a wellbore and generally includes an instrument housing incorporating a central processing unit (CPU) with memory for data storage and an external electrical resistance corrosion sensor. The corrosion sensor preferably consists of an extruded thin tube of the same or similar material as the wellbore tubing which will be monitored. The thin tube is supported at both its ends by an electrically insulating material which prevents galvanic corrosion between the instrument body and the corrosion sensor which could degrade the corrosion data. A reference element is manufactured from adjacent sensor materials and placed within the measurement element. Since both elements are made of the same material, the resistance changes relating to temperature variations occur at the same rate for both the sensing element and the reference element thereby eliminating the primary source of errors. The position of the measurement element is aligned with the flow of the fluid and parallel to the pipe to obtain similar flow characteristics on the sensing element as occurs within the pipe. The signal from the sensor is received by the resident CPU where it is stored in solid state memory for later retrieval. A separate temperature sensor is utilized to supply temperature data as well as to provide for compensation of second order temperature affects on the corrosion measurement. The storage of data at programmed time intervals allows the tool to store a history of metal loss which relates to the effects any corrosion inhibitors, corrosion inhibitor flow rates, temperature and density may have on the surrounding pipe. Analysis of the data retrieved by the downhole monitoring tool provides information concerning the optimum combination of elements to reduce corrosion rates within the wellbore.

Other objects, features, and advantages of the invention will be apparent from the following detailed description taken in connection with the accompanying drawings.

BRIEF DESCRIPTION OF THE DRAWING

The present invention will be more fully understood by reference to the following detailed description of a preferred embodiment of the present invention when read in conjunction with the accompanying drawing in which like reference characters refer to like parts throughout the views and in which:

FIG. 3 is an enlarged cross-sectional view of the instrument tube for the accumulation and storage of data;

FIG. 4 is an end view of the instrument tube;

FIG. 5 is a schematic wiring diagram of the instrument board; and

DETAILED DESCRIPTION OF A PREFERRED EMBODIMENT OF THE PRESENT INVENTION

Figure 1:
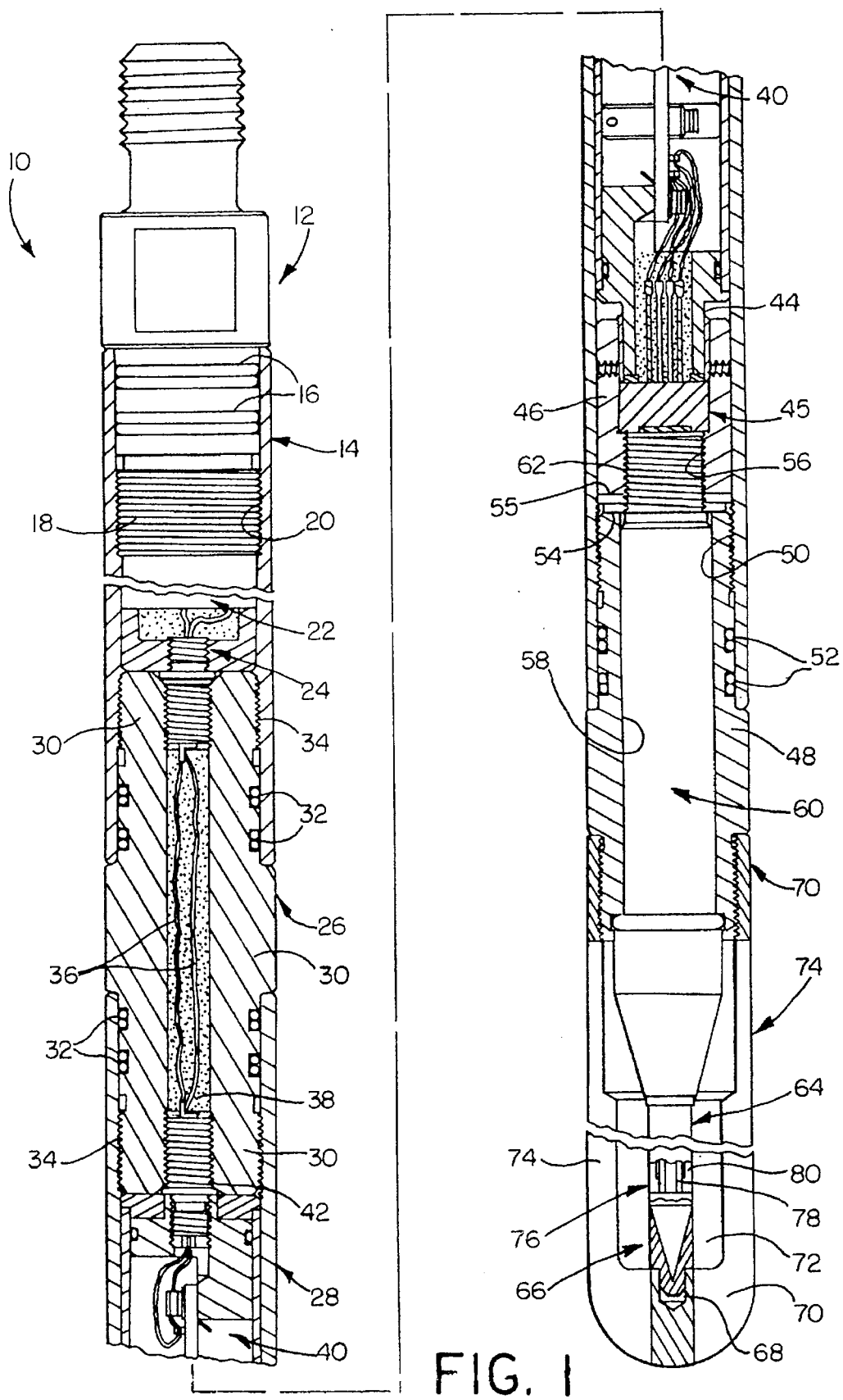
FIG. 1 is a cross-sectional view of a downhole corrosion monitoring tool embodying the present invention.
Figure 2:
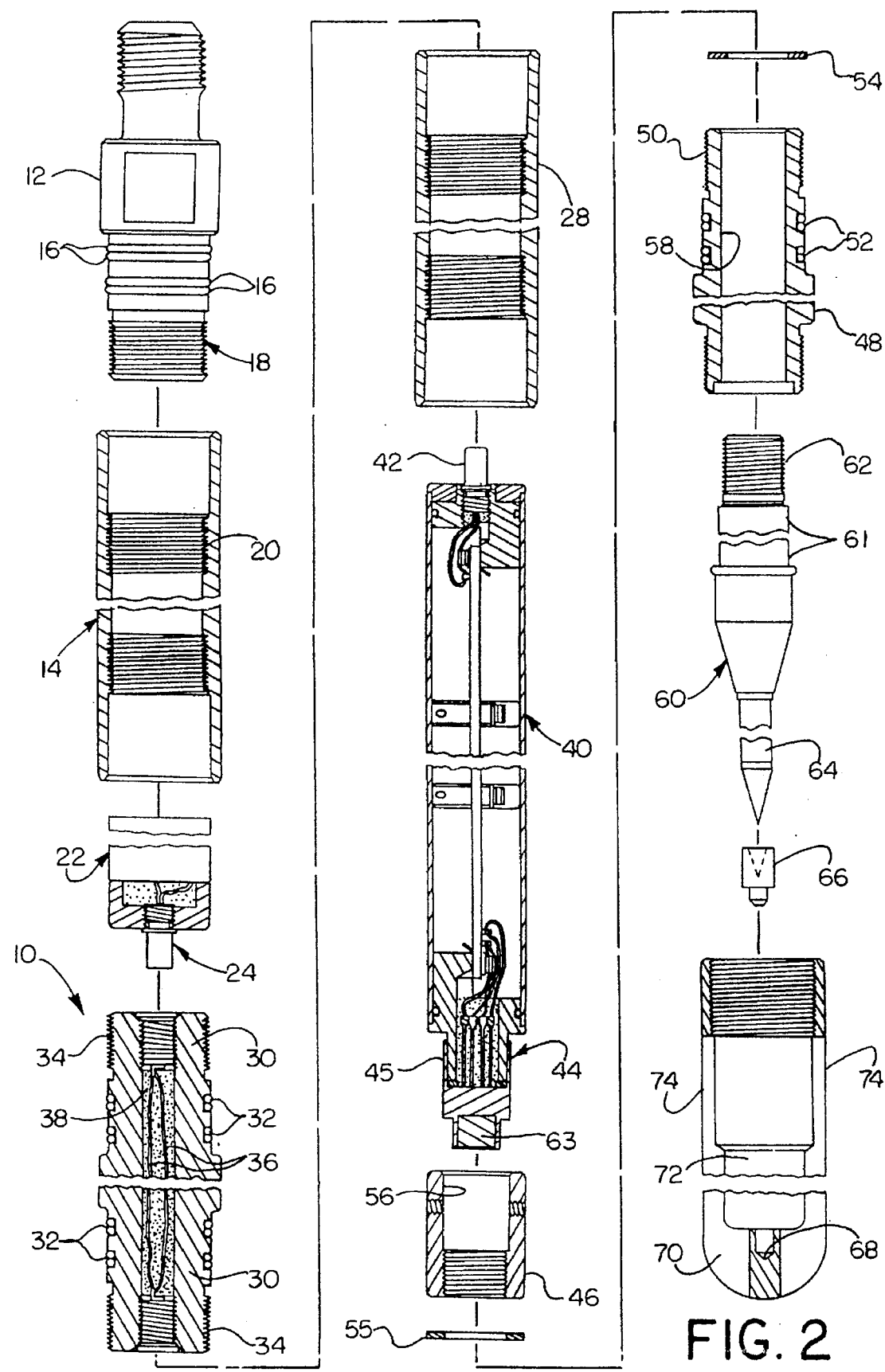
FIG. 2 is an exploded view of the corrosion monitoring tool.

Referring first to FIGS. 1 and 2, there is shown a corrosion monitoring tool 10 for collecting data on metal loss within a wellbore. Oil and gas or geothermal wells create corrosive environments because of the presence of carbonic acid or hydrosulfide acid within the well. Such environments, if left unchecked, can corrode drill pipes or production tubing within the well. The corrosion monitoring tool 10 of the present invention provides data on corrosion metal loss over an extended period of time. Analysis of the metal loss history can provide data on the effectiveness of corrosion inhibitors as they are introduced downhole. The monitoring tool 10 is a self-contained unit with battery power and memory storage so that the tool 10 may be positioned in the wellbore even at remote locations without the need for surface monitoring. After a predetermined period, the tool 10 may be retrieved from the well and the memory dumped for analysis of the data.

The corrosion monitoring tool 10 is a self-contained unit which is run into the well on a downhole carrier threadably connected to an upper coupling 12. The upper coupling 12 is matingly received within an upper end of a battery housing 14. The coupling 12 includes O-ring seals 16 which seal against the inner surface of the battery housing 14 and a threaded portion 18 which threadably connects to the inner threaded surface 20 of the battery housing 14. A replaceable battery assembly 22 is disposed within the housing 14 and includes at least one terminal 24 for connection to the monitoring instruments. An intermediate adapter assembly 26 isolates and connects the battery housing 14 to an instrument housing 28. The adapter 26 includes identical end portions 30 with O-ring seals 32 and threaded male connectors 34 for sealing connection to the battery housing 14 and the instrument housing 28. Lead lines 36 extend through an insulated central core 38 to deliver power from the battery 22 to the measuring and storage instrument.

The instrument housing 28 is threadably and sealingly connected to the adapter 26. An instrument assembly 40 (more clearly shown in FIG. 3) is received within the instrument housing 28. The instrument assembly 40 has a terminal 42 which connects to the lead lines 36 of the adapter 26. Mounted to the downhole end 44 of the instrument assembly 40 is a loading nut 46 which is also received within the instrument housing 28. A probe adapter 48 is threadably and sealingly received within the instrument housing 28 to enclose the instrument assembly 40. The probe adapter 48 includes a threaded male connector 50 and O-ring seals 52 which sealingly engage the inner surface of the instrument housing 28. Insulating washer 54 and thrust or load washer 55 are inserted between the loading nut 46 and the adapter 48. Both the loading nut 46 and the adapter 48 include axial passageways 56 and 58, respectively, through which a probe 60 can be inserted. The probe 60 has a seal/insulator 61 to electrically isolate the probe 60 from the adapter 48 upon insertion. A multi-prong plug 63 of the instrument assembly 40 mates with a probe connector 62. The threaded male connector 62 on the probe 60 is threadably received in the loading nut 46 such that the probe 60 is in contact with the downhole end 44 of the instrument assembly 40 which is electrically isolated from the instrument assembly 40 by insulator 45.

The probe 60 has a generally frusto-conical configuration with a probe element 64. A probe element insulator 66 is mounted to the element 64 and is matingly received within a downhole end 68 of a probe shield 70. The probe shield 70 threadably attaches to the probe adapter 48 to protect the probe element 64 from damage. In a preferred embodiment, the probe shield 70 includes openings 72 which facilitate the free flow of fluid across the probe element 64. The longitudinal supports 74 which form the cage of the probe shield 70 may be machined out of the same material as the borehole liner to act as a weight loss coupon to verify data obtained through the probe 60. The probe element insulator 66 insulates the probe 60 from the shield 70 and tool housing to prevent galvanic corrosion which may falsify corrosion readings. Accordingly, the probe is electrically isolated from all external housing elements of the tool 10 and is only connected to the instrument board and battery which are also electrically isolated from the tool housing. As a result, the tool 10 is capable of withstanding extreme pressures and temperatures of the wellbore yet the internal electrical components are electrically isolated from the housing.

The corrosion sensor forms a part of the probe element 64 and consist of a thin wall sleeve 76 made of the same material as the borehole liner to form the corrosion measurement element. An inner sleeve 78 formed of the same material as the outer sleeve 76 forms the reference element. The space 80 between the measurement element 76 and the reference element 78 is filled with an insulating material to maintain separation. A temperature sensor 82 is also mounted on the PC board of the instrument assembly 40 to provide a reference temperature reading during data accumulation.

Referring now to FIGS. 3 through 5, the instrument assembly 40 is shown in different views. The instrument assembly 40 includes an instrument tube 100 sealed at both ends by end caps 102 and 104. The end caps 102,104 also act as mounts for a PC board assembly 106 which extends the length of the tube 100. The board 106 is connected to the upper cap 102 by a fastener 108 and to the lower cap 104 by fastener 110. The board 106 is positionally maintained by a plurality of spacers 112 disposed within the tube 100 and receiving the board 106. Extending through the upper cap 102 is the plug connector 42 which is in electrical communication with the board 106 through wires 114. Power for the instrument assembly 40 is provided by the battery 22 through the plug connector 42 to the board 106. The downhole end 44 of the instrument assembly 40 incorporates a multi-pronged plug 116 which extends through the lower cap 104. The prongs 118 are electrically isolated by an insulation material 120 and are hard-wired to the board 105 through wires 122. The prongs 118 provide the electrical connectivity between the measurement sensor 76, the reference sensor 78 and the instrument tube assembly 40 carried within the tool 10. As a result, the CPU and memory of the corrosion monitoring tool 10 are carried within the tool 10 along with the power source 22 for operation of the tool 10 independent of any surface support to collect data on the corrosion rates within the wellbore.

Figure 6:
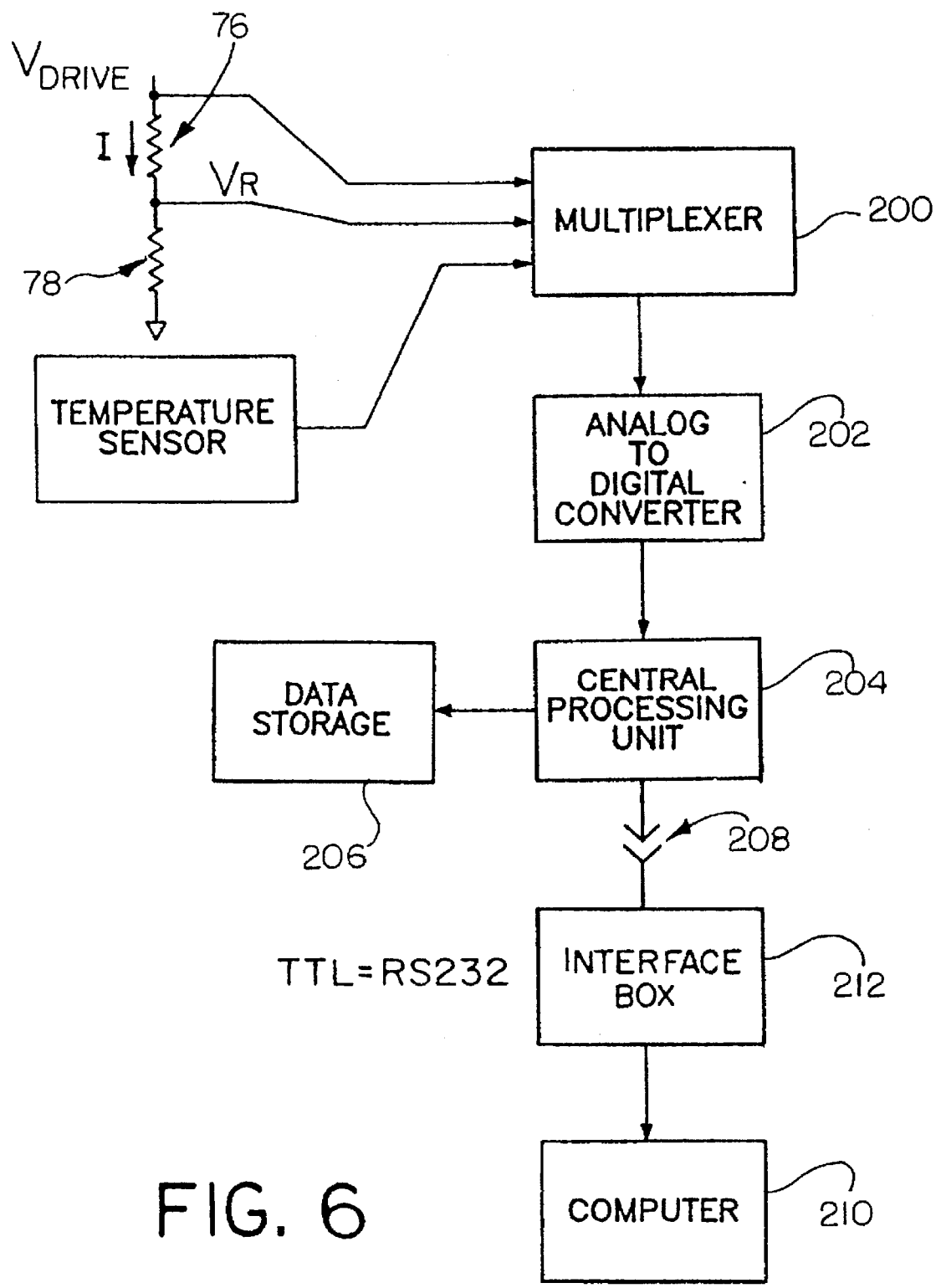
FIG. 6 is a flow chart embodying the corrosion monitoring tool of the present invention.

Operation of the corrosion monitoring tool 10 is schematically diagrammed in the flow chart of FIG. 6. A current I is formed by applying a battery voltage $V_{DRIVE}$ across the series resistance of the measurement sensor 76 plus the resistance of the reference element 78. The voltage developed across the measurement sensor 76 is $V_M$ and the voltage developed across the reference element 78 is $V_R$. The loss of metal from the measurement sensor 76 is determined from the ratio of $V_M/V_R$. As metal is lost from the measurement sensor 76 the resistance of the measurement sensor 76 will increase yielding an increase to $V_M$. This increase in $V_M$ causes a change in the ratio determined by $V_M/V_R$. This ratio can then be put into an equation:

$$\text{metal loss} = (\text{measurement sensor thickness}/2) \times (2000 - 1960/(V_M/V_R))$$

which yields the amount of metal that has been lost from the surface of the measurement sensor 76. In this preferred embodiment the ratio $V_M/V_R$ is the data which is stored in memory 206 for downloading into an external computer 210.

The voltages developed across the measurement sensor 76, the reference element 78, and the temperature sensor 82 are selected one at a time by multiplexer 200 and converted to digital signals by the analog-to-digital converter 202. The CPU 204 computes the $V_M/V_R$ ratio and computes the temperature from the signal supplied by the temperature sensor 82 and stores these values in data storage 206.

The CPU 204 performs the above steps on a programmable periodic basis, typically sixty minutes, and stores each set of data values sequentially in data storage 206. This cycle continues until the battery 22 runs out of energy or the test is ended by retrieving the tool 10 from the wellbore. Upon retrieval, the tool 10 is disassembled and instrument tube 40 is removed from the assembly. The instrument tube 40 is connected to the levels converter box 212 which also supplies operating power to the instrument tube 40. Data can then be downloaded from the instrument tube 40 to an external computer 210 for processing and analysis. Accordingly, the present invention provides an accurate means of collecting data on corrosion within a well without the need for surface support or monitoring by providing a self-contained system for accumulating the corrosion data at specified intervals.

The foregoing detailed description has been given for clearness of understanding only and no unnecessary limitations should be understood therefrom as some modifications will be obvious to those skilled in the art without departing from the scope and spirit of the appended claims.

What is claimed is:

1. An apparatus for measuring environmental parameters within a wellbore having metal material there.., said apparatus comprising:

an elongated housing positionable within the wellbore and including a downhole end;

detecting means disposed within said housing for detecting the environmental parameters within the wellbore proximate said housing, said detecting means including at least one sensor for measuring the loss of metal material within the wellbore; and data storage means in communication with said detecting means for storing data information communicated by said detecting means, said data storage means being disposed within said housing.

2. The apparatus as defined in claim 1 and further comprising means for supplying electrical power for operation of said detecting means and data storage means.

3. The apparatus as defined in claim 2 wherein said power means includes at least one battery disposed within said housing and electrically connected to said detecting means and data storage means.

4. The apparatus as defined in claim 2 wherein said electrical power of operation of said detecting means and data storage means is supplied from the surface through a wireline tool attached to said housing.

5. The apparatus as defined in claim 2 wherein said detecting means includes a temperature sensor and said sensor for measuring the loss of metal within the wellbore, said sensors being disposed at said downhole end of said housing.

6. The apparatus as defined in claim 5 wherein said at least one sensor for measuring the loss of metal includes a primary corrosion sensor and a secondary reference corrosion sensor, said detecting means measuring the electrical resistance of said primary and secondary sensors such that said metal loss is determined through comparison of a ratio of electrical resistance across said primary sensor and electrical resistance across said secondary sensor.

7. The apparatus as defined in claim 6 wherein said primary corrosion sensor includes an outer sleeve formed of a similar metal material as the metal material within the wellbore and said secondary corrosion sensor incudes an inner sleeve coaxially mounted within said outer sleeve, whereby said outer sleeve is exposed to the wellbore environment.

8. The apparatus as defined in claim 7 wherein said data storage means includes a central processing unit and a memory unit, said central processing unit communicating with said detecting means to process and store data from said detecting means onto said memory unit.

9. The apparatus as defined in claim 8 wherein said central processing unit and said memory unit are disposed within an instrument assembly housed within said housing.

10. The apparatus as defined claim 9 wherein said instrument assembly includes a connector for providing communication between said memory unit and an independent processing unit at the surface such that said data stored on said memory unit may be downloaded to said independent processing unit.

11. An apparatus for measuring environmental parameters within a wellbore having metal material therein, said apparatus comprising:

an elongated housing positionable within the wellbore and including a downhole end;

a detecting probe disposed within said downhole end of said housing such that said probe is exposed to the wellbore environment, said probe including a primary corrosion sensor and a secondary reference corrosion sensor for determining a loss of metal material within the wellbore, said probe being electrically isolated from said elongated housing of said tool;

data storage means disposed within said housing in electrical communication with said detecting probe, said data storage means including a central processing unit and a memory unit, said central processing unit receiving downhole environment data from said detecting probe and storing said data on said memory unit; and means for supplying electrical power for operation of said detecting probe and said data storage means, said power supply means being disposed in said housing in electrical communication with said detecting probe and said data storage means whereby said apparatus may be positioned in the wellbore for independent operation collecting data on the wellbore environment.

12. The apparatus as defined in claim 11 wherein said power supply means includes at least one battery disposed within said housing in electrical communication with said detecting probe and said data storage means.

13. The apparatus as defined in claim 11 wherein said detecting probe further comprises a temperature sensor, said primary corrosion sensor, said secondary reference corrosion sensor and said temperature sensor supplying data on the wellbore environment to said data storage means.

14. The apparatus as defined in claim 13 wherein said primary corrosion sensor includes an outer sleeve formed of a metal material similar to the metal material within the wellbore and said secondary reference corrosion sensor includes an inner sleeve coaxially mounted within said outer sleeve, whereby said outer sleeve is exposed to the wellbore environment.

15. The apparatus as defined in claim 14 and further comprising a probe shield forming a part of said housing, said probe shield being formed of a metal material similar to the metal material within the wellbore thereby forming a weight loss coupon exposed to the wellbore environment, said weight loss coupon providing means for verifying corrosion rates within the wellbore.

16. The apparatus as defined in claim 14 wherein said central processing unit measures the electrical resistance of said primary and secondary sensors such that said metal loss is determined through comparison of a ratio of electrical resistance across said primary sensor and electrical resistance across said secondary reference sensor.

* * * * *